United States Patent
Hyun et al.

(10) Patent No.: US 10,940,096 B2
(45) Date of Patent: Mar. 9, 2021

(54) ENTERAL FEEDING AIR PURGE SYSTEM AND METHOD

(71) Applicant: MEDELA HOLDING AG, Baar (CH)

(72) Inventors: Dongchul D Hyun, Brea, CA (US);
Matthew Hyon, Brea, CA (US);
Michael Fleury, Brea, CA (US)

(73) Assignee: MEDELA HOLDING AG, Baar (CH)

(*) Notice: Subject to any disclaimer, the term of this patent is extended or adjusted under 35 U.S.C. 154(b) by 149 days.

(21) Appl. No.: 15/819,426

(22) Filed: Nov. 21, 2017

(65) Prior Publication Data

US 2018/0263855 A1  Sep. 20, 2018

Related U.S. Application Data

(63) Continuation of application No. 15/478,260, filed on Apr. 24, 2017, now abandoned.

(60) Provisional application No. 62/318,750, filed on Apr. 5, 2016.

(51) Int. Cl.
*A61J 15/00* (2006.01)
*A61J 9/00* (2006.01)
*A61M 5/14* (2006.01)

(52) U.S. Cl.
CPC ....... *A61J 15/0026* (2013.01); *A61J 15/0076* (2015.05); *A61J 15/0096* (2013.01); *A61J 9/00* (2013.01); *A61J 15/0003* (2013.01); *A61M 2005/1403* (2013.01)

(58) Field of Classification Search
CPC .............. A61J 15/0076; A61J 15/0096; A61M 2005/1403
See application file for complete search history.

(56) References Cited

U.S. PATENT DOCUMENTS

| | | | | |
|---|---|---|---|---|
| 3,610,241 A | * | 10/1971 | LeMarie | A61M 5/1782 604/407 |
| 4,456,152 A | * | 6/1984 | Young | G01F 11/023 222/309 |
| 4,518,387 A | * | 5/1985 | Murphy | A61M 5/422 604/115 |
| 4,683,916 A | * | 8/1987 | Raines | F16K 15/148 137/854 |
| 4,740,203 A | * | 4/1988 | Hoskins | A61M 25/10182 604/191 |
| 4,944,726 A | * | 7/1990 | Hilal | A61M 5/007 222/389 |
| 6,270,481 B1 | * | 8/2001 | Mason | A61M 5/1424 604/181 |
| 9,522,237 B2 | * | 12/2016 | Alheidt | A61M 5/31515 |
| 10,086,132 B2 | * | 10/2018 | Hauswald | A61M 5/1452 |
| 2011/0087173 A1 | * | 4/2011 | Sibbitt, Jr. | A61B 10/0233 604/207 |
| 2016/0296423 A1 | * | 10/2016 | Ruda | A61J 15/0076 |

\* cited by examiner

*Primary Examiner* — William R Carpenter
(74) *Attorney, Agent, or Firm* — McDonnell Boehnen Hulbert & Berghoff LLP

(57) ABSTRACT

A system for purging air from a feeding line is set forth. The system includes a charging device configured to selectively provide an air charge in the system. A restricting tubing can be located between the charging device and a delivery tube. The restricting tubing can be configured to tunably limit the air charge delivered from the charging device to the feeding line through the delivery tube.

19 Claims, 8 Drawing Sheets

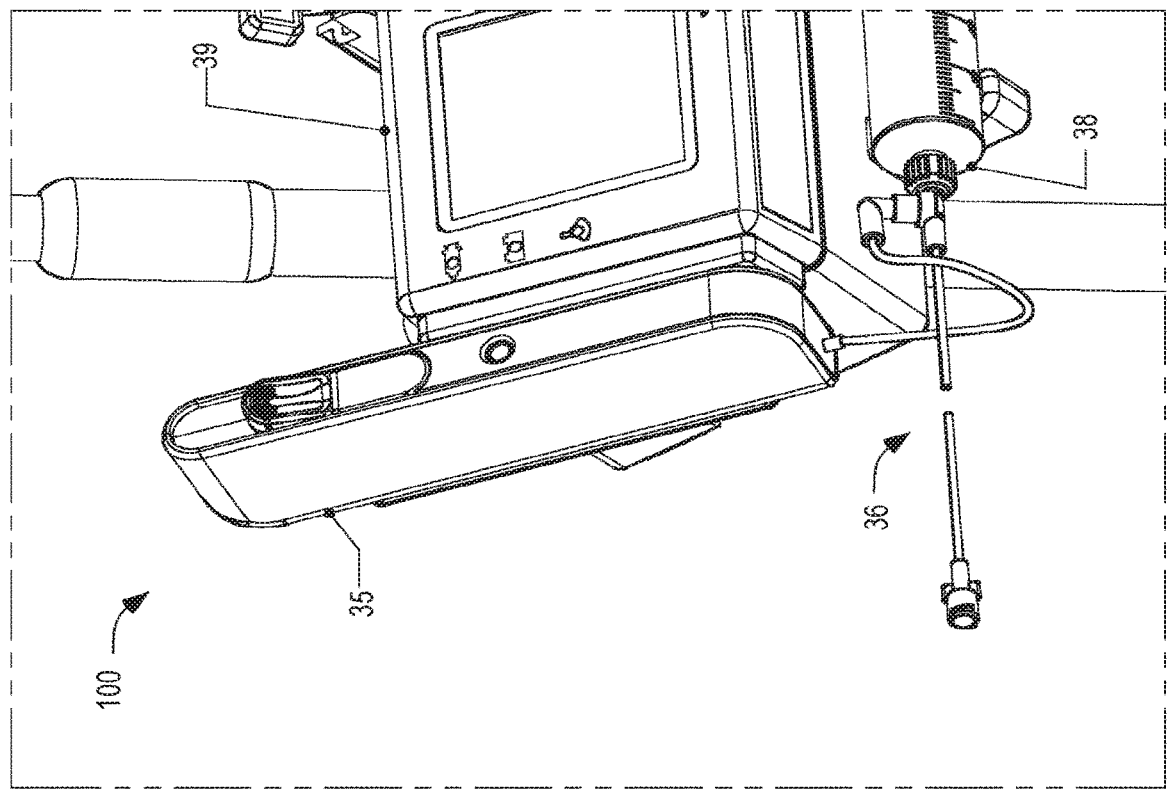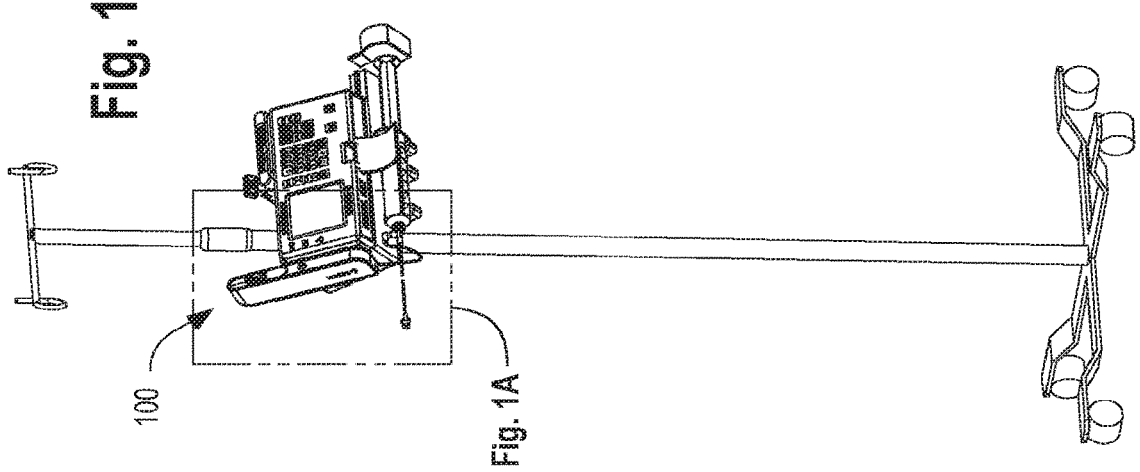

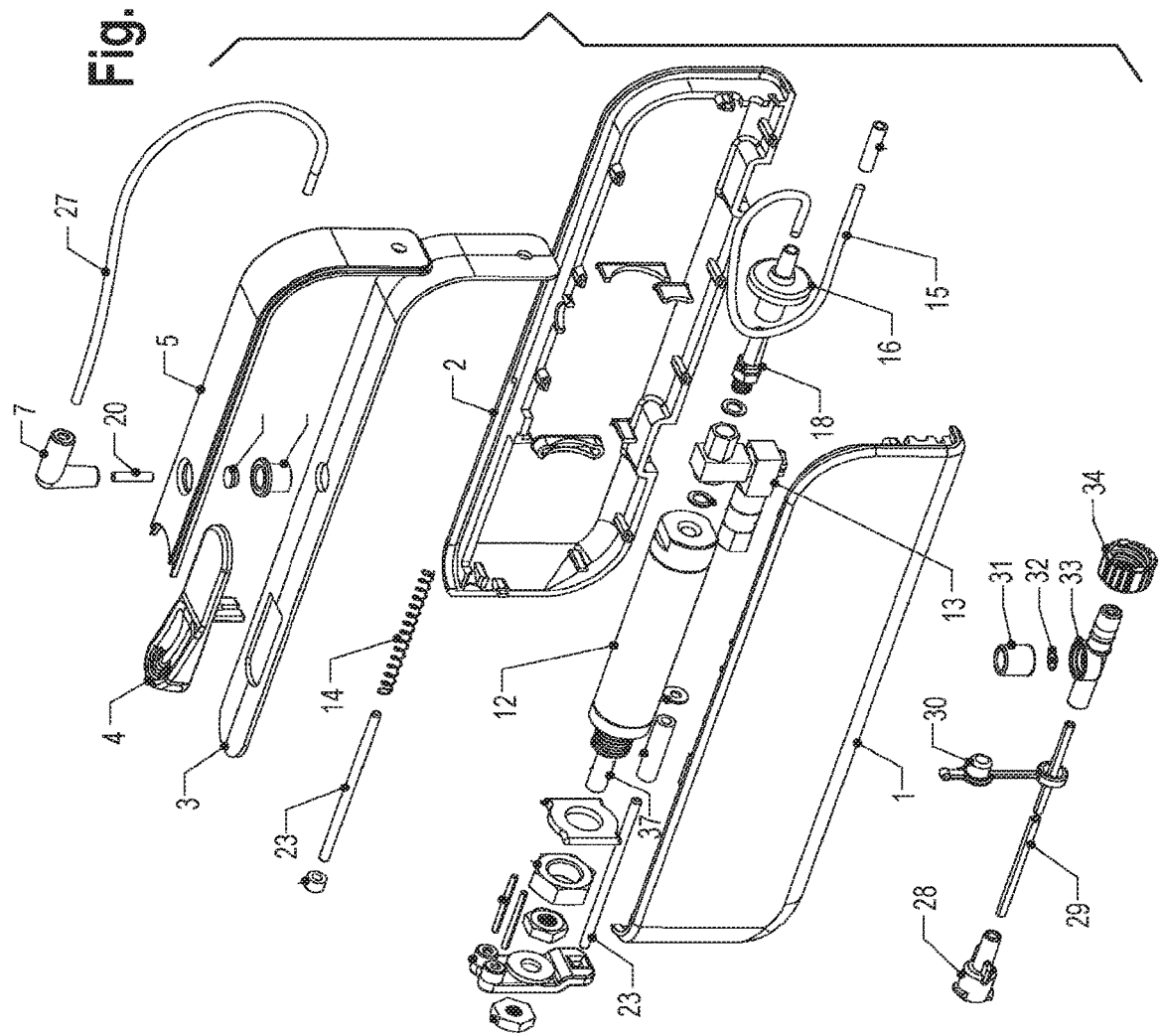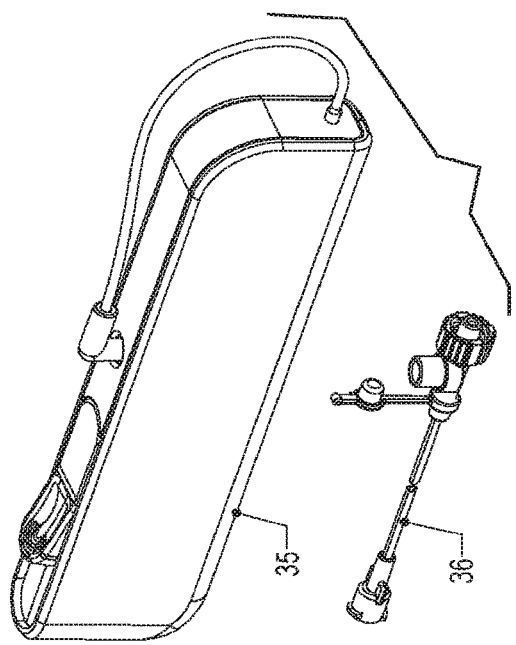

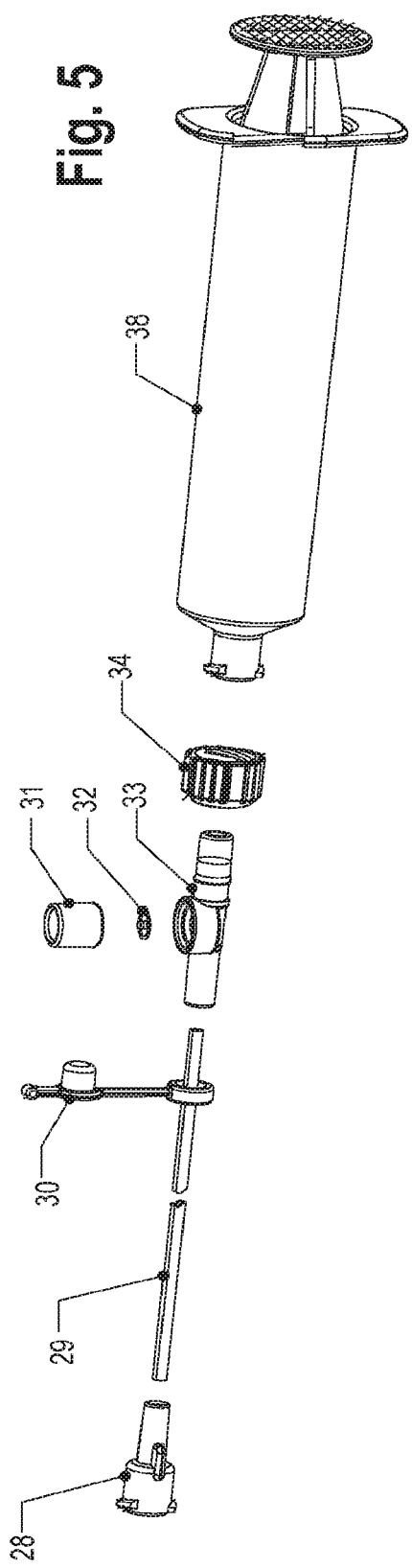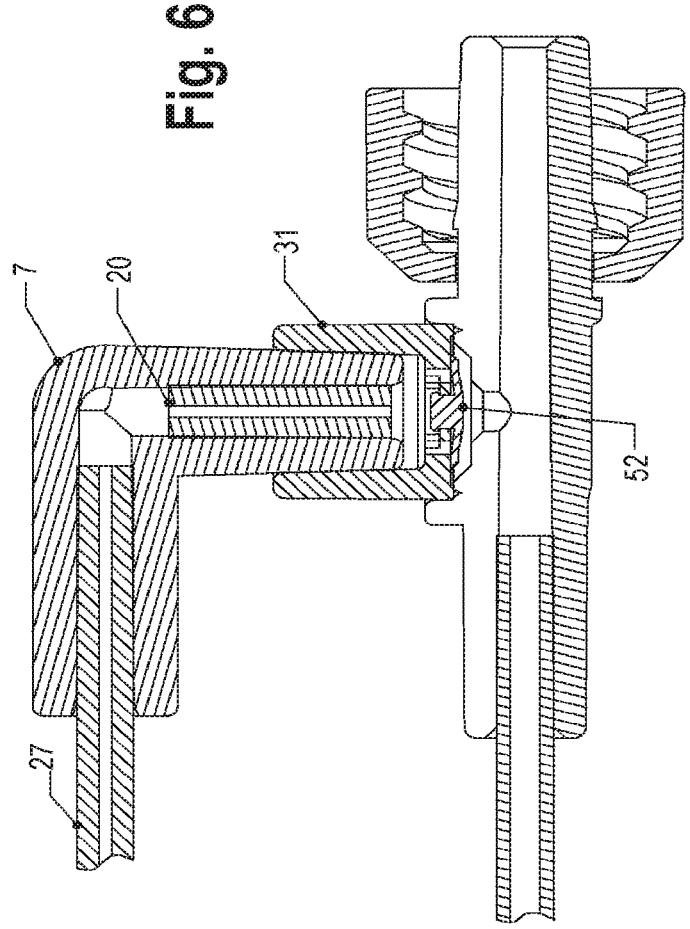

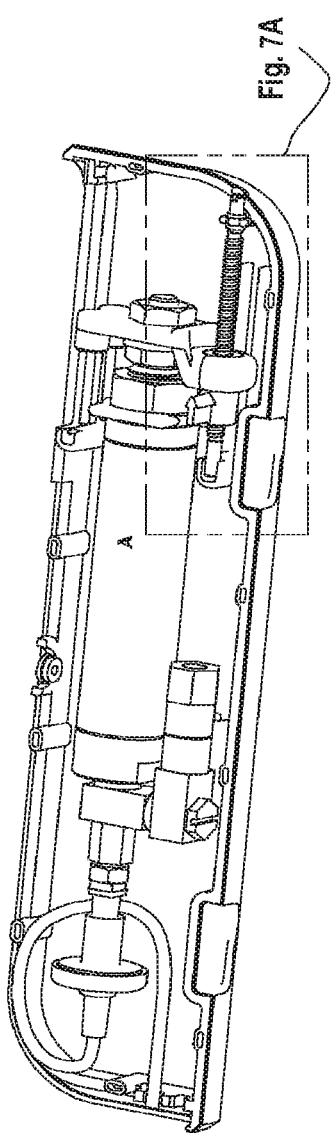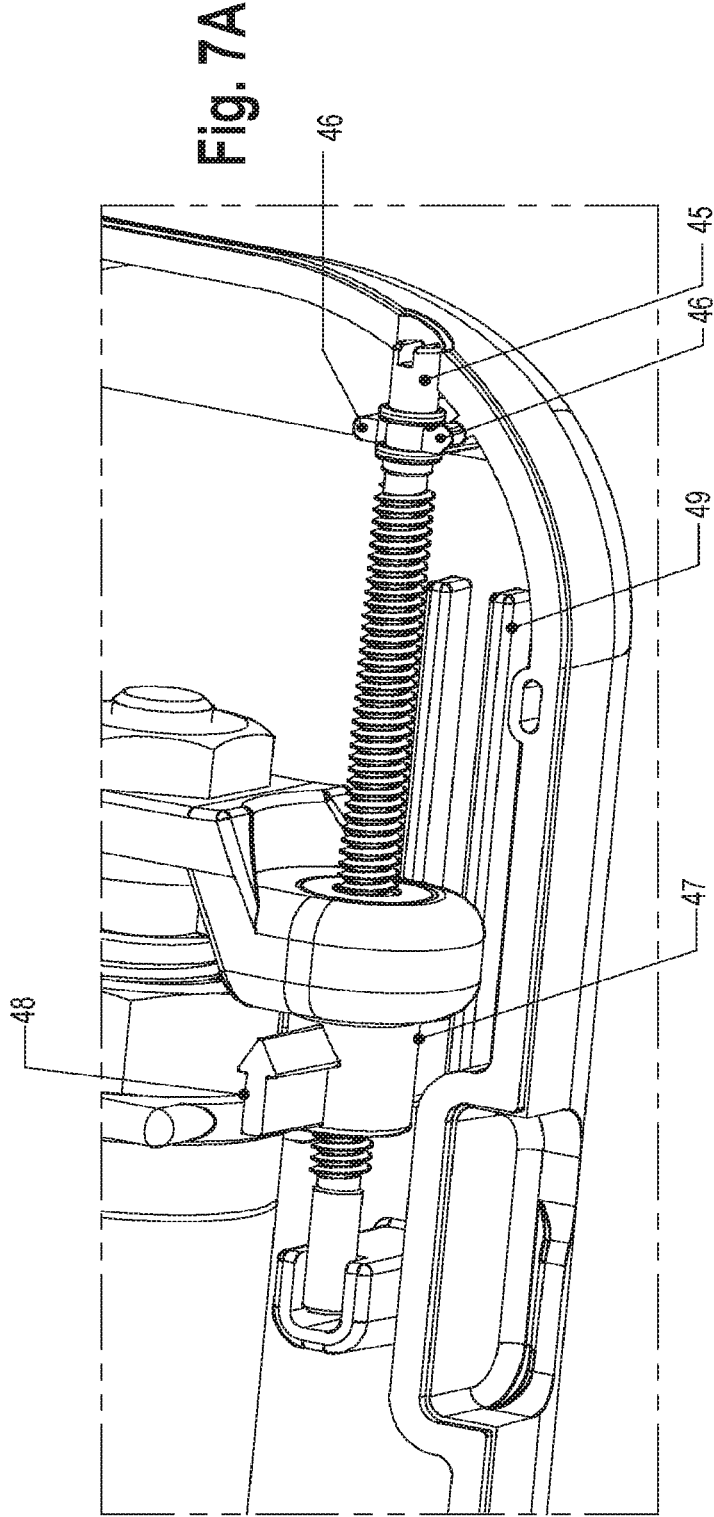

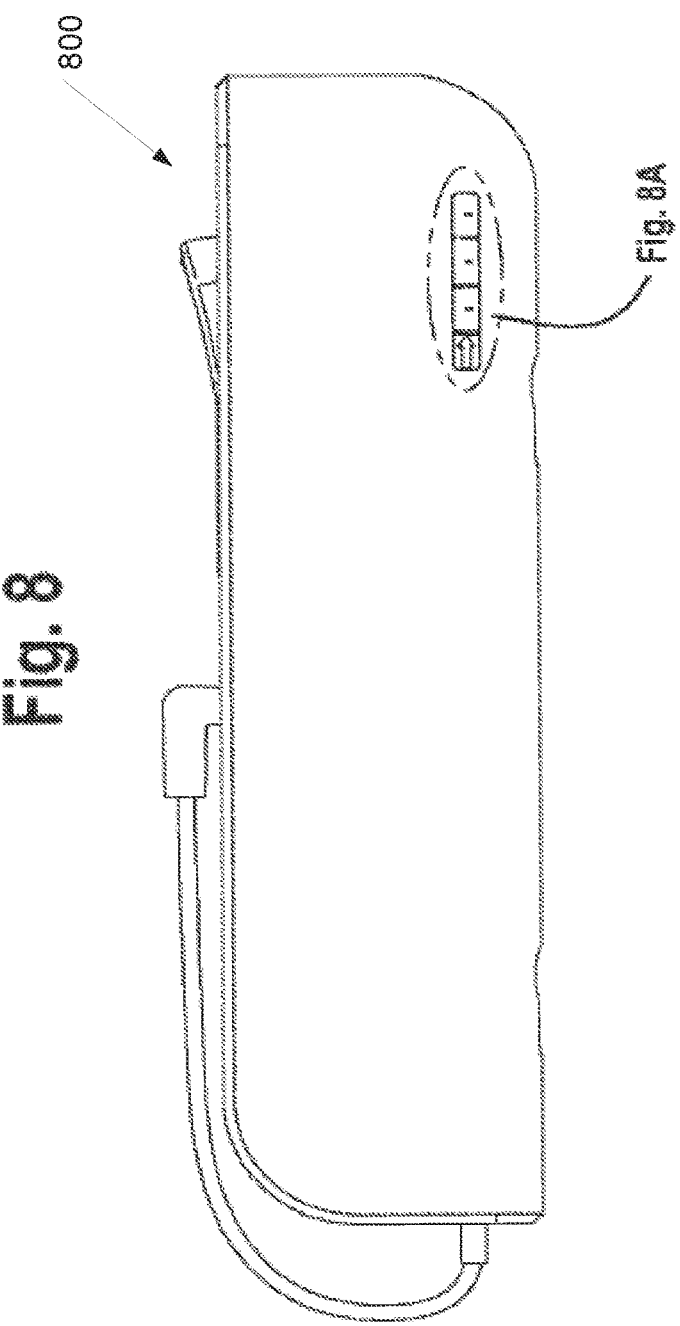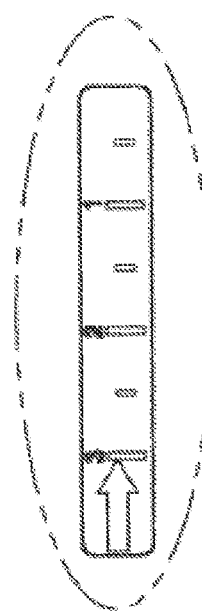

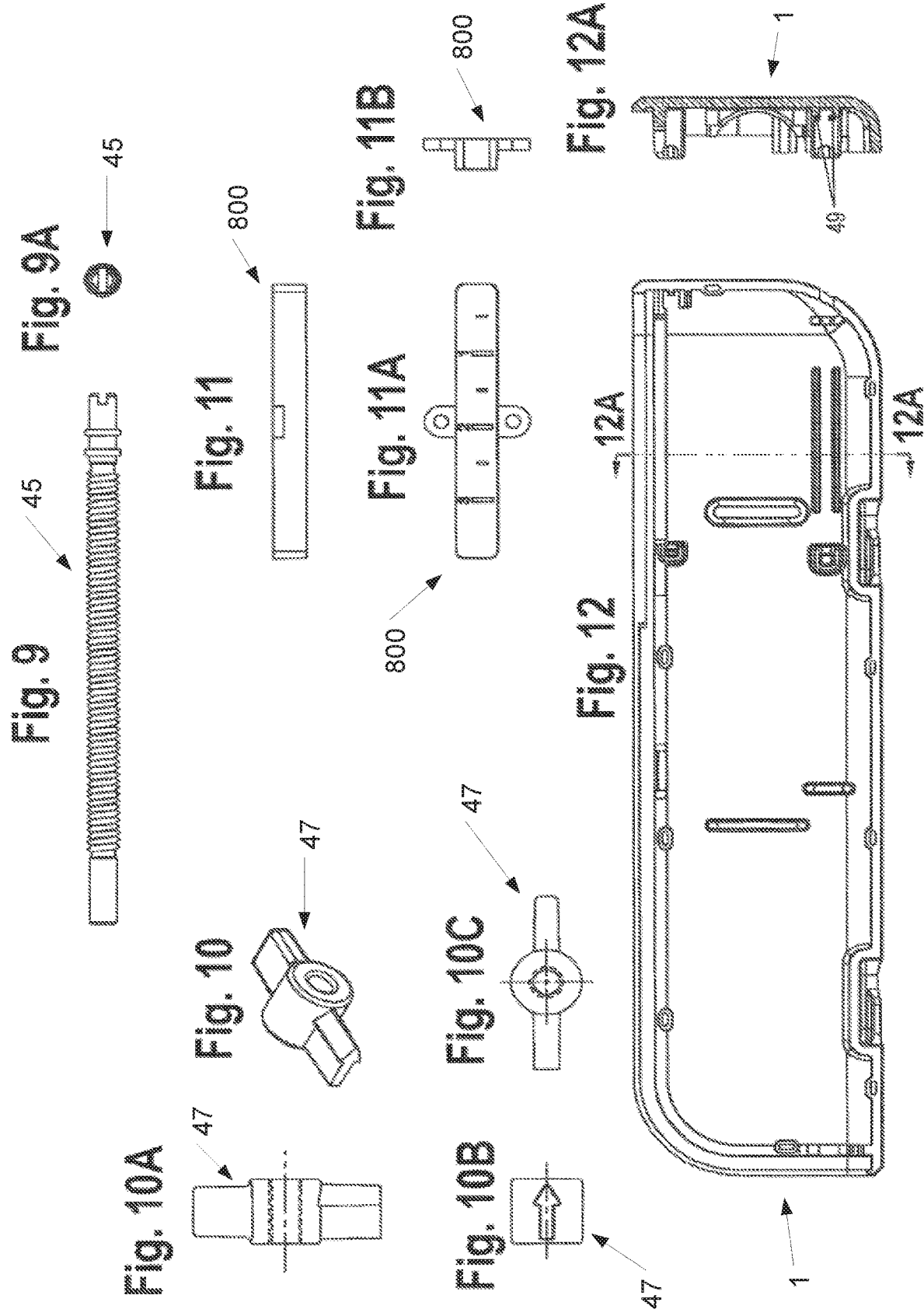

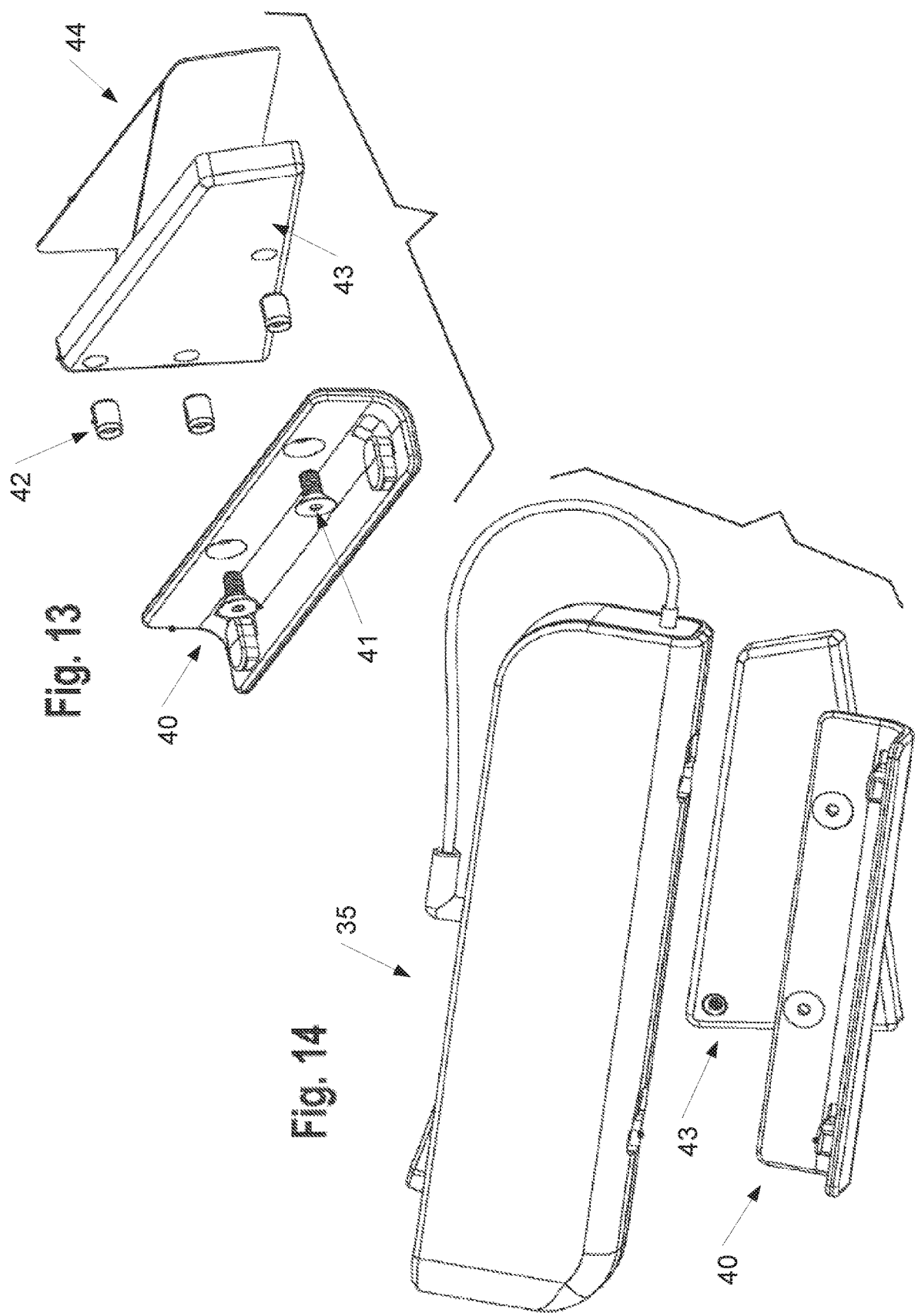

ENTERAL FEEDING AIR PURGE SYSTEM AND METHOD

CROSS-REFERENCE TO RELATED APPLICATIONS

This application is a continuation of U.S. application Ser. No. 15/478,260 filed on Apr. 4, 2017, which claims priority to U.S. provisional application No. 62/318,750 filed on Apr. 5, 2016. The entire disclosure contents of these applications are herewith incorporated by reference into the present application.

TECHNICAL FIELD

The present disclosure relates generally to a purging system that addresses a problem in hospitals concerning feeding via enteral feeding devices.

BACKGROUND

High-risk newborns are babies that have undeveloped responses to sucking reflexes or are otherwise unable to receive nutrition orally. The established method of feeding these newborn babies in the NICU environment is to place an enteral feeding tube into the baby's stomach orally or nasally. The enteral feeding tube can be connected to a food source by one of the following methods: 1) a direct connection can be made to a syringe filled with milk (or other nutritional liquid) from which food is dispensed using a gravity method, or 2) a tube can be connected to an extension set that connects to a syringe driven by a pump containing liquid feed. The present disclosure is directed to a system that provides an improvement in enteral feeding using either of these methods.

A common extension set for feeding newborn babies can be formed of an extruded tube of any suitable material such as PVC. On both ends of the tube are suitable tubing extensions, such as connectors, suitably attached to the tube by bonding, for example, or by another suitable method, that provide a leak-tight fluid path from a syringe to the baby. At the end of the enteral feed, when the pump cycle has finished, an extension set can contain a small amount of remaining, or residual, nutritional liquid, such as, for example, approximately 1 ml to 2 ml of remaining liquid.

Currently there is no generally accepted way to deliver this remaining liquid to the baby. As a result, the remaining liquid is typically discarded or bolus fed into the infant by attaching an additional syringe and manually injecting air into the tube to flush the remaining fluid into the baby. Neither of these options provides a suitable solution for delivering liquid remaining at the end of a feeding delivery cycle to babies.

There are problems with both of these options for handling the remaining liquid at the end of the feeding session. With 8 feeds per baby per day, an average sized NICU could be discarding 60 to 70 liters of high value enteral feeding liquid per year. There is also evidence that when human breast milk is delivered in this manner, the milk that remains in the extension set is substantially higher in fat value than the delivered milk. This is thought to be due to properties in fat, such as low density, that causes the fat to concentrate in the extension tubing. Additionally, the practice of manually injecting air into the extension set via a syringe is highly variable, and could add the enteral fluid to the baby at a much higher rate than what was originally intended, which can lead to other undesirable effects.

SUMMARY

In accordance with the principles herein, a purge system for delivering the remaining liquid to the baby, while avoiding both high rate and variable delivery of the liquid as well as waste, is set forth. In an embodiment, the purge system can include a first part and a second part. The first part can include an additional port added to an extension set syringe connector. The second part of the purge system is a purge device which can connect to the additional port, if desired, and to an enteral feeding line, or extension set, via a suitable connection.

In operation, the care-giver or nurse can activate and releases an initiating device, such as, for example, a thumb-slide. The thumb slide can selectively enable delivery of an air charge that causes a fixed volume of filtered air to travel through a tube connected to the extension set.

An air filter is provided for filtering the air in the system. A restrictor tubing can be attached to the air filter. The restrictor tubing has the effect of pushing out the remaining liquid in the tube slowly, stopping the effect of pressure connected with the air charge as the air reaches the end of the feeding tube. The restrictor tube, or tubing, of the purge device is formed of a suitable hospital grade material and allows for a tunable, custom setting for air delivery from the purge device to the extension tube. Use of the system will enable consistent full nutritional delivery and free up valuable time for care-givers. If desired, a knob, or other mechanical or electrical adjustment device, could be added to adjust the air delivery volume of the system.

Additionally, if desired, an instruction to adjust the air delivery can be received remotely by a suitable system, such as an enteral feeding pump system incorporating the purge system, or remaining liquid system, herein, from an EMR system. Further, the purge system can also be used as an infusion device. To this end, data associated with the infusion process can be tracked and/or captured during the infusion process by a remote system, or by a system including an purge system and an enteral feeding pump system.

BRIEF DESCRIPTION OF THE DRAWINGS

FIGS. 1 and 1A illustrate perspective and detailed views, respectively, of an exemplary embodiment of a purge system 100 constructed in accordance with the principles herein;

FIG. 4 illustrates a perspective view of an exemplary embodiment of a purge system 400;

FIG. 4A illustrates an exploded view of the purge system shown in FIG. 4;

FIGS. 5 and 6 illustrate an exemplary extension set adapter assembly that can be used in conjunction with a purge system constructed in accordance with the principles herein;

FIGS. 7 and 7A illustrate another embodiment shown generally at 700 of an exemplary purge device which is adjustable as to the amount of air expelled during a stroke or cycle;

FIGS. 8 and 8A illustrate an exemplary embodiment shown generally at 800;

FIGS. 9 and 9A are front and side views, respectively, of a threaded rod that can be incorporated within a purge system constructed in accordance with the principles herein;

FIGS. 10, 10A, 10B, and 10C are isometric, top, front, and right side views, respectively, of a positive stop that can be incorporated within a purge system constructed in accordance with the principles herein;

FIGS. 11, 11A, and 11B are top, front, and right side views, respectively, of parts shown in Figure FIGS. 12 and 12A are orthographic drawings of exemplary adjustable stop system components that can be incorporated into any of the exemplary purge systems herein if desired;

FIG. 13 shows an exemplary mounting bracket; and

FIG. 14 illustrates the attachment features of the exemplary mounting bracket to an exemplary purge device housing.

DETAILED DESCRIPTION

Figure 2:
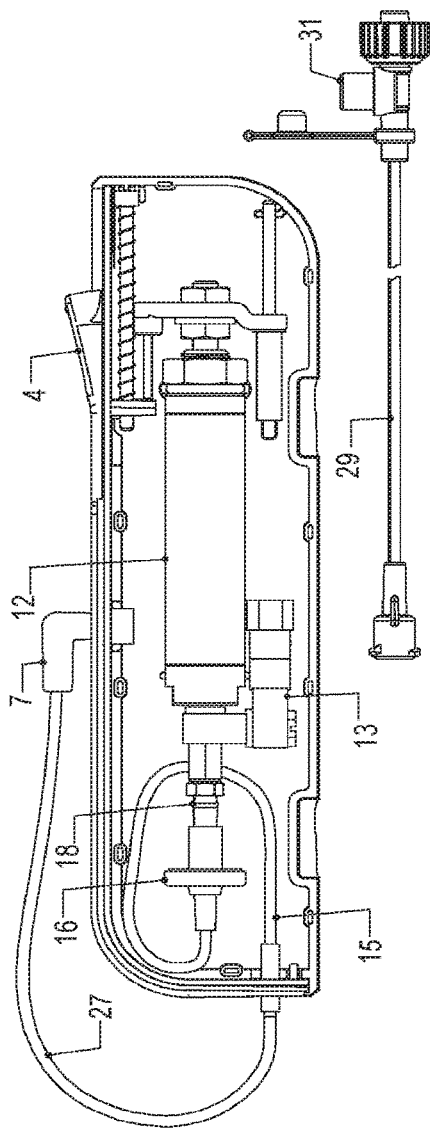
FIG. 2 illustrates a front perspective view of an exemplary embodiment of a purge system 100 and associated extension set shown in FIG. 1 with a face plate of the purge system removed.

FIG. 1 shows an exemplary embodiment of a purge system, shown generally at 100. The purge system 100 can include a purge device 35 removably connected to an extension set assembly 36 and to an enteral feeding pump system 39. The extension set 36 is selectively connected to a syringe 38 of the enteral feeding pump system 39. The device 35 and extension set assembly 36 can be connected as shown, with the extension set directly connected to a syringe mounted on a syringe pump, or using any other suitable connection. FIGS. 1 and 1A show a perspective view of an exemplary embodiment illustrating one way in which the device 35 and extension set 36 can be connected, with the extension set in place on a syringe 38 which is mounted in a syringe pump 39.

FIG. 2 shows interior components of an exemplary purge system, wherein a front plate is removed, and with a suitable extension set 36. Individual components shown in Figure Components of FIG. 2, such as housing components, can be formed of a suitable material, such as an injection-molded plastic, such as ABS, or any other suitable plastic; whereas, port 7 can be at least partially formed of a softer material such as PVC, or other suitable material, which aids in creating an air-tight seal where port 7 is selectively and removably inserted into or otherwise contacts to form a connection with a seal cup 31 of the extension set 36. A slide 4 can be provided and spring-loaded in order to disconnect the slide 4 and its additional friction from the operation of an air cylinder 12 of the system.

A suitable filter 16, such as a 0.2 micron filter, can be included for anti-bacteria purposes, if desired. A check valve 13, or other suitable device or assembly, can be provided to force air flow from the air cylinder 12 to the restrictor tubing 15, either directly or indirectly. Air flow proceeds from the restrictor tubing 15 through tubing 27, and is delivered to a port 31 from the port 7 when the system is connected to the extension set 36. The air flow continues to through an extension tube 29 of the extension set 36.

An exemplary valve, such as an umbrella valve 32, shown in FIG. 4A, can be embedded in a port 31 of an extension set 36 associated with or provided with the system. This valve 32 can then allow air through from the purge device 35, but prevent liquid from exiting out from the extension set assembly 36 of the purge system.

The inner diameter (ID) of tubing 27 of the system can be small in order to cut down on air compression effects, but is generally configured to be larger than restrictor tubing 15, which then acts as a throttle valve between the air cylinder 12 and the tubing 27.

Figure 3:
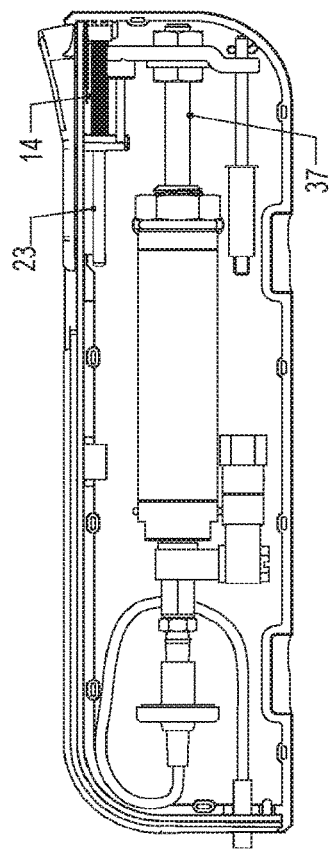
FIG. 3 illustrates the exemplary purge system of FIG. 2 with an initiating device shown in a load position.

FIG. 3 shows the thumb-slide 4, being moved forward to a stop, cracking open a check valve 13, and compressing a spring 14 which is guided by a steel rod 23. This action of the thumb-slide 4 thus results in a plunger 37 extending out of the air cylinder 12.

Figure 3A:
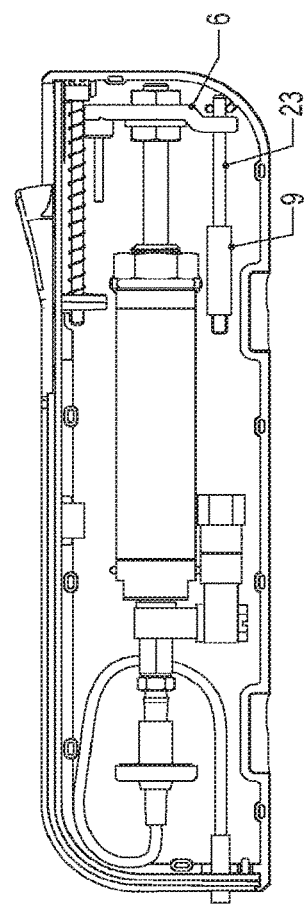
FIG. 3A illustrates a return path for the initiating device of FIG. 3.

FIG. 3A illustrates an exemplary embodiment with the thumb-slide 4 being released and returning immediately to its original normal position while the plunger 37 of the air cylinder 12 remains extended. A spring (not shown) internal to the air cylinder 12, or other suitable reciprocating device, pulls the plunger back. As the plunger returns, the check valve 13 closes, forcing air in the cylinder 12 to flow only through a fitting 18, the air filter 16, and the restrictor tubing 15. The air exits the main device into a tube 27, shown in FIG. 2, and is finally dispensed through the fittings 7 & 31 to the extension tube 29, as shown in FIG. 2, thereby pushing the enteral fluid out into a feeding tube.

FIGS. 5 and 6 show an exemplary extension set adapter assembly 36. FIG. 5 also shows exemplary components of an extension set 36, including the umbrella valve 32, also shown in FIG. 6, which can be fixated into the seal cup 31. The seal cup can then be suitably connected, such as via ultrasonic-welding, for example, to the adapter body 33. One end of the adapter body 33 can be selectively connected to an adapter cap 34, which can be secured to a syringe 38, while another end of the adapter body 33 can be fitted to the extension tube 29 of the extension set 36. The extension tube 29 is fitted into a feeding tube adapter 28. A seal 30 can be provided for inserting into the seal cup 31 when the extension set 36 and purge system 35 are not connected.

FIG. 6 shows an exemplary embodiment of how the assembly can look when in use, ready to purge the extension set. The air-tight fit between the tip connector 7 and the seal cup 31 that can provide the air flow from tubing 27 to the extension tube 29 of the extension set 36 can be configured so that it can be held by friction and easily engaged and removed by hand. A tube connector insert 20 can be bonded inside the tube connector 7 in order to reduce the effects of air compression.

FIGS. 7 and 7A show another embodiment of an exemplary purge device which is adjustable as to the amount of air expelled during a stroke or cycle. Instead of a steel pin, a threaded rod 45 can be provided to guide the cylinder plunger through the connector plate, which can contain a suitable bearing, such as an engineering plastic bearing 46 formed of, for example PEEK (polyetheretherketone). The rod can be threaded through a positive stop 47 which can contain an arrow 48 or other index line and can be prevented from rotating by means of an extended flange that can be captured between two guide rails 49. The guide rails 49 can be molded into the case back, if desired. When rotated by a small screwdriver, the positive stop can move axially, allowing the arrow to correspond with index marks placed on a clear window part as shown in FIGS. 8 and 8A.

FIG. 7A also shows the stepped attachment features of the threaded rod 45 which can fit into sockets 46 molded into the purge device case.

FIGS. 9 through 12 are orthographic drawings of the adjustable stop system components. FIGS. 9 and 9a are front and side views respectively of part 45. FIGS. 10 thru 10c are isometric, top, front, and right side views respectively of part 47. FIGS. 11 thru 11b are top, front and right side views of the part shown in FIG. 8. FIG. 12 is a front view of part 1. FIG. 12A is a section view of part 1 showing the rails, detail 49.

With an adjustable stop and large enough air cylinder, small volume feeds can be accomplished in this embodiment by simply filling an appropriately sized extension set with enteral feeding fluid and using the purging device to deliver the small volume of enteral feeding fluid to the infant directly, without being incorporated between an enteral feeding pump and an extension set. The enteral feeding fluid can be filtered as needed. This embodiment could be accomplished without setting up a syringe pump. The purge device can be connected to the extension tube set and then disposed right inside the incubator with no electricity involved. The purge device could be contained inside a disposable plastic bag, but could operate the same way as described above.

FIGS. 13 and 14 show an exemplary embodiment including components of an exemplary mounting bracket assembly which can allow the purge device to be removably secured to the side of an enteral syringe pump 39 (shown in FIGS. 1 and 1A), which is typically where the purge device would be mounted. To this end, suitable connector openings 50 can be provided anywhere on the purge system 35 for selectively and removably connecting the mounting bracket to the purge system. However, it can also be easily removed from the bracket of the mounting bracket assembly and set in any convenient place near the enteral syringe pump. Threaded inserts 42 can be press fit into the pump attachment plate 43 which can have a high strength two-sided tape 44 applied to it for attaching to a pump 39, or any other suitable attachment material or assembly. Flat head screws 41 attach the mounting bracket 40 to the pump attachment plate 43. Other suitable connecting assemblies are contemplated herein.

While exemplary embodiments of the present disclosure are provided herein, various changes and modifications can be made without departing from the spirit and scope of the disclosure. The scope of the disclosure includes numerous combinations of components and substitutes therefor know in the art and used for purposes indicated in the disclosure, and all changes that come within the meaning and range of equivalents are intended to be embraced therein. For example, variations in the combinations, forming and/or any other features described in the present disclosure are within the spirit and meaning thereof.

We claim:

1. A system for purging air and liquid from a feeding line comprising:
   a purge device comprising an air cylinder configured to initiate an air charge in the system and an adjustable stop system, wherein the air cylinder comprises a plunger and a slide located on an outer surface of the housing, wherein the slide is configured to move the plunger from a first retracted position to an extended position, wherein moving the plunger from the first retracted position to the extended position opens a valve to activate the air cylinder to allow air flow therethrough;
   a restrictor tubing disposed between the purge device and a tubing;
   wherein the adjustable stop system is configured to adjustably limit the air charge delivered from the purge device to a feeding line through the tubing, the adjustable stop system comprising a positive stop mounted to a rod, wherein the plunger abuts the positive stop when in the retracted position; and
   a first spring coupled to a second slide and a second spring internal to the air cylinder, wherein movement of the second slide forward to a stop is configured to compress of the first spring and move the plunger from the retracted position to the extended position, and wherein compression of the second spring is configured to move the plunger from the extended position to the retracted position.

2. The system of claim 1, further comprising an extension set assembly configured to attach to the purge device and to connect the purge device to an enteral feeding pump system.

3. The system of claim 2, wherein the extension set assembly comprises:
   an adapter body configured to connect to the purge device, the adapter body including a seal cup; and
   an extension tube configured to connect the adapter body to a feeding tube.

4. The system of claim 3, further comprising a removable port disposed on the purge device, wherein the seal cup is configured to connect to the removable port on the purge device via the tubing.

5. The system of claim 4, wherein an umbrella valve is positioned within the seal cup, the umbrella valve being configured to allow air through from the purge device and to prevent a liquid from exiting out from the extension set assembly.

6. The system of claim 4, wherein an inner diameter of the tubing is larger than an inner diameter of the restrictor tubing.

7. The system of claim 1, wherein the valve is a check valve and wherein the slide is configured to open the check valve.

8. The system of claim 1, further comprising a mounting bracket assembly secured to the purge device, the mounting bracket assembly configured to secure the purge device to an enteral syringe pump.

9. A system for purging air and liquid from a feeding line comprising:
   a housing;
   an air cylinder located within the housing and comprising a plunger, the aft cylinder configured to initiate an aft charge in the system;
   a removable port located on an outer surface of the housing;
   a slide located on an outer surface of the housing, the slide configured to move the plunger from a first retracted position to an extended position, wherein moving the plunger from the retracted first position to the extended position opens a valve to activate the aft cylinder to allow air flow therethrough;
   a restrictor tube disposed between the air cylinder and a tubing tube;
   an adjustable stop system configured to adjustably limit the air charge delivered from the air cylinder to a feeding line through the tubing, the adjustable stop system comprising a positive stop mounted to a rod, wherein the plunger abuts the positive stop when in the retracted position; and
   a first spring coupled to a second slide and a second spring internal to the air cylinder, wherein movement of the second slide forward to a stop is configured to compress of the first spring and move the plunger from the retracted position to the extended position, and wherein compression of the second spring is configured to move the plunger from the extended position to the retracted position.

10. The system of claim 9, wherein the slide is a thumb slide.

11. The system of claim 9, wherein the plunger is disposed within a cavity of the air cylinder.

12. The system of claim 9, wherein the valve is a check valve, wherein the slide is configured to open the check valve.

13. The system of claim 9, further comprising a mounting bracket assembly secured to the housing, the mounting bracket assembly configured to secure the system to an enteral syringe pump.

14. A system for purging air and liquid from a feeding line comprising:
    a housing;
    an air cylinder located within the housing and comprising a plunger, the aft cylinder configured to initiate an aft charge in the system;
    a removable port located on an outer surface of the housing;
    a slide located on an outer surface of the housing, the slide configured to move the plunger from a first retracted position to an extended position, wherein moving the plunger from the retracted first position to the extended position opens a valve to activate the air cylinder to allow air flow therethrough;
    a restricting tubing disposed between the aft cylinder and a tubing;
    an adjustable stop system configured to adjustably limit the aft charge delivered from the air cylinder to a feeding line through the tubing, the adjustable stop system comprising a positive stop mounted to a rod, wherein the plunger abuts the positive stop when in the retracted position;
    an extension set assembly configured to attach to the removable port in the housing and configured to connect the system to an enteral feeding pump system; and
    a first spring coupled to a second slide and a second spring internal to the air cylinder, wherein movement of the second slide forward to a stop is configured to compress of the first spring and move the plunger from the retracted position to the extended position, and wherein compression of the second spring is configured to move the plunger from the extended position to the retracted position.

15. The system of claim 14, wherein the extension set assembly comprises:
    an adapter body configured to connect to the removable port, the adapter body including a seal cup; and
    an extension tube configured to connect the adapter body to a feeding tube.

16. The system of claim 15, wherein an umbrella valve is positioned within the seal cup, the umbrella valve configured to allow air through from the air cylinder and to prevent a liquid from exiting out from the extension set assembly.

17. The system of claim 1, wherein the rod of the adjustable stop system comprises a threaded rod configured to be threaded through the positive stop.

18. The system of claim 1, wherein opening the valve causes the air charge to flow from the air cylinder into the restrictor tubing, and wherein moving the plunger from the extended position to the retracted position closes the valve.

19. The system of claim 1, wherein the second slide is a thumb slide.

* * * * *

UNITED STATES PATENT AND TRADEMARK OFFICE
CERTIFICATE OF CORRECTION

PATENT NO. : 10,940,096 B2  
APPLICATION NO. : 15/819426  
DATED : March 9, 2021  
INVENTOR(S) : Dongchul D Hyun et al.

Page 1 of 1

It is certified that error appears in the above-identified patent and that said Letters Patent is hereby corrected as shown below:

On the Title Page

Item (54) and in the Specification, Column 1, Line 1: please delete "AIR"

In the Claims

Claim 1, Column 5, Line 53: please delete "first"
Claim 1, Column 5, Line 54: please delete "first"
Claim 9, Column 6, Line 40: please replace aft with --air--
Claim 9, Column 6, Line 45: please delete "first"
Claim 9, Column 6, Line 47: please delete "first"
Claim 9, Column 6, Line 48: please replace aft with --air--
Claim 14, Column 7, Line 14: please replace the aft cylinder with --the air cylinder--
Claim 14, Column 7, Line 14: please replace an aft with --an air--
Claim 14, Column 7, Line 19: please delete "first"
Claim 14, Column 7, Line 21: please delete "first"
Claim 14, Column 7, Line 24: please replace aft with --air--
Claim 14, Column 7, Line 27: please replace aft with --air--

Signed and Sealed this  
Twenty-second Day of June, 2021

Drew Hirshfeld  
*Performing the Functions and Duties of the*  
*Under Secretary of Commerce for Intellectual Property and*  
*Director of the United States Patent and Trademark Office*